(12) United States Patent
Yu (10) Patent No.: US 10,426,704 B2
(45) Date of Patent: Oct. 1, 2019

(54) PRE-DOSED APPLICATORS AND PACKAGING THEREFOR

(71) Applicant: Centrix, Inc., Shelton, CT (US)

(72) Inventor: Pengguang Yu, Branford, CT (US)

(73) Assignee: Centrix, Inc., Shelton, CT (US)

( * ) Notice: Subject to any disclaimer, the term of this patent is extended or adjusted under 35 U.S.C. 154(b) by 136 days.

(21) Appl. No.: 15/690,399

(22) Filed: Aug. 30, 2017

(65) Prior Publication Data
US 2018/0064607 A1   Mar. 8, 2018

Related U.S. Application Data

(60) Provisional application No. 62/384,091, filed on Sep. 6, 2016.

(51) Int. Cl.
*A61J 3/00* (2006.01)
*A61F 13/40* (2006.01)
*A61J 1/14* (2006.01)

(52) U.S. Cl.
CPC .............. *A61J 3/00* (2013.01); *A61J 1/1412* (2013.01); *A61M 35/006* (2013.01); *A61M 2209/045* (2013.01); *A61M 2209/06* (2013.01); *A61M 2210/0618* (2013.01)

(58) Field of Classification Search
CPC ............ A61J 3/00; A61J 1/145; A61J 1/1412; A61M 35/006; A61M 2209/045; A61M 2209/06; A61M 2210/0618; A61M 35/003; A61B 17/24
See application file for complete search history.

(56) References Cited

U.S. PATENT DOCUMENTS

| | | | |
|---|---|---|---|
| 5,947,986 A * | 9/1999 | Lewis | A61F 15/001 604/1 |
| 6,387,068 B1 * | 5/2002 | Naughton | A45D 29/007 206/210 |
| 6,971,879 B2 | 12/2005 | Discko, Jr. | 433/163 |
| 8,714,353 B2 * | 5/2014 | Hohlbein | A61C 19/02 206/362 |
| 2006/0063128 A1 | 3/2006 | Dragan | 433/89 |

* cited by examiner

*Primary Examiner* — David J Walczak
(74) *Attorney, Agent, or Firm* — Fattibene and Fattibene LLP; Paul A. Fattibene (57) ABSTRACT

A container holding pre-dosed applicators for applying a material. The container holds the pre-dosed applicators upright with the absorbent end of the pre-dosed applicator contacting an absorbent pad on the bottom of the container containing a solution with a desired material to be applied. The absorbent pad holds a predetermined quantity of material for dosing the applicators. The packaging and dosing of the applicators can be performed concurrently facilitating manufacturing and making packaging more efficient and cost effective.

12 Claims, 6 Drawing Sheets

PRE-DOSED APPLICATORS AND PACKAGING THEREFOR

RELATED APPLICATION

This application claims the benefit of United States Provisional Application No. 62/384,091 filed Sep. 6, 2016, which is incorporated herein by reference.

FIELD OF THE INVENTION

The present invention relates in general to a pre-dosed applicator for applying a material, and particularly to a pre-dosed applicator for applying a hemostatic agent.

BACKGROUND OF THE INVENTION

Many materials such as chemicals and medicaments are applied with an applicator. Typically, the material to be applied is contained in bulk form, such as a bottle or jar into which the applicator is dipped. This is often inconvenient and results in potential contamination. Applicators that provide a single use are often desired. Of even more convince are pre-dosed singe use applicators. There have been attempts to pre-dose applicators with a liquid material. However, over a period of time the liquid may dissipate reducing shelf-life or longevity of the pre-dosed applicator. A pre-dosed application is discloses in United States Patent Application Publication US 2006/0063128 entitled "Pre-Dosed Applicator and Applicator System Including Dispensing of Multi-part Dental Materials" invented by Dragan, herein incorporated by reference. Therein disclosed is a pre-dosed applicator that has a dried material thereon placing the material in an inactive stable state until reactivated. While this was an improvement and increased shelf-life or longevity there is a need for a pre-dosed applicator that does not need to be reactivated and that has long shelf-life or longevity.

SUMMARY OF THE INVENTION

The present invention improves packaging and pre-dosing of applicators. A container holds pre-dosed applicators for applying a material. The container holds the pre-dosed applicators upright with the absorbent end of the pre-dosed applicator contacting an absorbent pad on the bottom of the container. The absorbent pad holds a predetermined quantity of material for dosing the applicators. The predetermined quantity of material may be adjusted to control the degree of material saturation of the pre-dosed applicator. The packaging and dosing of the applicators may be performed concurrently facilitating manufacturing.

Accordingly, it is an object of the present invention to package pre-dosed applicators more efficiently.

It is an advantage of the present invention that the degree of material saturation of the pre-dosed applicators can be controlled.

It is a feature of the present invention that an absorbent pad is placed at the bottom of a container and contacts an absorbent end of an applicator.

These and other objects, advantages, and features will become more readily apparent in view of the following detailed description.

DETAILED DESCRIPTION OF THE PREFERRED EMBODIMENTS

A packaging system is utilized to dose the pre-dosed applicators concurrently with packaging of the applicators. This embodiment of the present invention greatly reduces production time by dosing and packaging the pre-dosed applicators in a single procedure.

Figure 1:
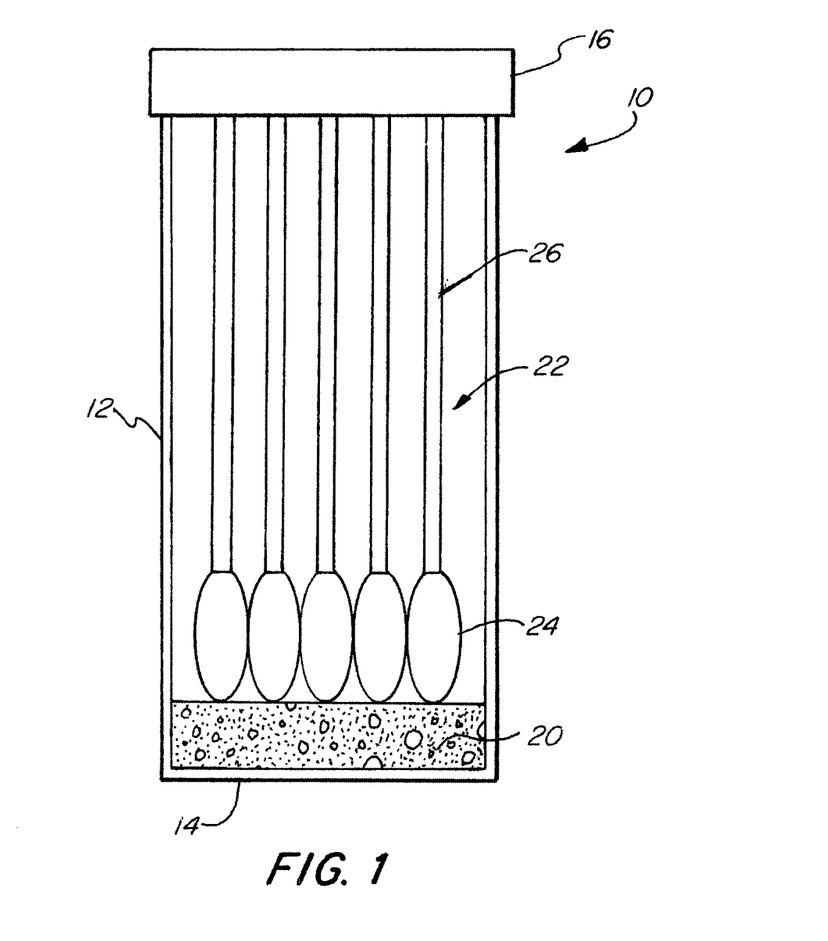
FIG. 1 schematically illustrates a container for making and packaging the pre-dosed applicators of an embodiment of the present invention.

FIG. 1 illustrates an embodiment of the present invention. In FIG. 1, the packaged pre-dosed applicators 10 are illustrated. A container 12 holds a plurality of applicators 22 having an absorbent end 24 and a handle 26. The absorbent end 24 maybe made of any absorbent material, such as woven or wrapped cotton, foam, flock, or bristles. Such woven or wrapped cotton applicators are often sold under the trademark Q-Tip®. The absorbent end 24 may also be placed on each end or only a single end of the handle 26. The container 12 has a bottom 14 and a top covered by a lid 16. The lid 16 may be hingedly attached to the container 12 and provides a waterproof seal. The container 12 may also have its top covered by a removable plastic or foil seal. The container may also have its inner lid attached in such a way that the inner lid stays on and tightly attached to the container while the outer lid is removed. The inner lid may have an opening through which the applicators 22 can be taken out.

An absorbent pad 20 is placed adjacent to the bottom 14 of the container 12. A solution containing the material of which the pre-dosed applicators 22 are to be dosed is placed on the absorbent pad 20. During packaging, when the non-dosed applicators 22 are placed within the container 12 and the absorbent ends 24 are placed in contact with the absorbent pad 20 containing the material, the material in the absorbent pad 20 is absorbed by the absorbent end 24 for forming the pre-dosed applicators 22. The absorbent pad 20 can also be in a compressed dry form. Non-dosed applicators 22 can then be placed in the container 12 and the solution can then be injected or placed into the container 12 to form the pre-dosed applicators 22.

In this way the packaging and a dosing of the pre-dosed applicator 22 is accomplished concurrently greatly facilitating manufacturer of packaged pre-dosed applicators 10. This improves manufacturing efficiencies and lowers cost.

The present invention may be used as an improvement of or replacement for a styptic pencil when dosed with a antihemorrhagic agent. The styptic pencil is a hard bar made of aluminum sulfate, packed in a shape of a stick. The styptic material acts as an antihemorrhagic agent that promotes hemostasis or stops bleeding. A styptic works by contracting tissue to seal injured blood vessels and often contains an astringent.

The invention is a method developed to produce packaged pre-dosed applicators in one easy and continuous manufacturing operational or process in the most cost-effective manner. In the process an absorbent applicator, such as a Q-tip brand applicator, is soaked with aluminum sulfate or other antihemorrhagic agent and preserved in a designated condition such as very wet, wet, damp and dry. The method or process of pre-dosing the applicator is completed simultaneously or concurrently with the packaging process.

The method or process is extremely useful for production involved with handling volatile or poisonous reagents, such as phenol. The disclosed process dramatically reduces handling procedures and therefore reduces chance for human contact with dangerous substances. It is also a safe, reliable and controllable process to ensure a safe working environment.

The method or summary of operational procedure is indicated below:

1. Place an absorption disc at the bottom of a container.
2. Add X or a predetermined amount of aluminum sulfate solution at a certain concentration into the container.
3. Insert Y number or a plurality of Q-tips or other applicators into the container, so that the container is full.
4. Close the lid of the container.

An alternative method or procedure is to swap step 2 with step 3, that is to first put the applicators into the container and then add the solution. This alternative method or procedure is useful when the applicators length is close to the length of the height of the container, because the applicators may have a tendency to float up for a period of time before they absorb the solution.

A container with a lid may be used. A preferred container may have its inner diameter at the bottom being 0.75 inches, with an inner height of approximately 2.82 inches. Suitable containers are generally cylindrically shaped and made of plastic with an attached cap.

An absorbent pad is placed in the bottom of the container. In one preferred configuration, the absorbent pad 20 may be a cotton paper with thickness of approximately 0.81 mm or approximately 0.032 inches and is used as an absorption material. The paper may be cut by stamping to form a disc with a 0.75 inch diameter. A 28.77% aluminum sulfate solution was prepared using distilled water.

Wetness of the absorbent pad may be defined into four levels, they are:

Very wet: water drips when hanging
Wet: water film is visible at surface, but no dripping
Damp: no water film at surface, but feels wet
Nearly dry: not feel wet, or almost dried out The absorbent pad or cotton disc serves as a reservoir, which holds a solution in a sufficient amount or quantity during an anticipated storage time period. The solution contained in the absorbent pad is released as needed and absorbed into the absorbent end of the pre-dosed applicator or Q-tips. Depending on the wetness level, the amount of solution needed for dosing the absorbent pad or cotton disc may be determined according to the solution absorption chart in Example 1.

EXAMPLE 1

Absorbent Pad or Paper Disc Solution Absorption Rate
Cotton paper, 0.81 mm thick, 19 mm in a diameter

| Wetness level | Amount of 28.77% aluminum sulfate solution (grams) |
| --- | --- |
| Very wet | 0.39 |
| Wet | 0.29 |
| Damp | 0.23 |
| Dearly dry | 0.17 |

The wetness of the pre-dosed applicator can be defined into four levels, they are:

Very wet: water drips when hanging
Wet: water film is visible at surface, but no dripping
Damp: no water film at surface, but feels wet
Nearly dry: not feel wet, or almost dried out An applicator with a consistent absorbent end, such as a Q-tip brand applicator, which size and qualities are usually very similar or identical among a batch should be used.

Depending on the wetness level desired, the amount of solution needed for dosing the absorbent end of the pre-dosed applicator may be determined according to the applicator absorbent end solution absorption chart in Example 2 below.

EXAMPLE 2

Applicator Absorbent End Solution Absorption Chart
Q-Tip Brand Applicator, Commercial Grade

| Wetness level | Amount of 28.77% aluminum sulfate solution (grams) |
| --- | --- |
| Very wet | 0.21 |
| Wet | 0.14 |
| Damp | 0.11 |
| Dearly dry | 0.07 |

The container, as described above, can hold 12 Q-tip brand applicators.

Once the wetness level desired is determined and the characteristic of the applicator end, such as a Q-tip brand applicator, is chosen, the amount of solution can be calculated.

For a pre-dosed applicator the number of grams of solution required is equal to, (Number of absorbent pads)×(weight of solution for each absorbent pad)+(number of applicators with absorbent ends)×(weight of solution for each absorbent end).

As an example, for a wet pre-dosed applicator using four absorbent pads, as in Example 2, and twelve Q-tip brand applicators, as in Example 1, the weight of solution required is indicated by the formula 1 below.

$$W=4\times0.29 \text{ g}+12\times0.14 \text{ g}=2.84 \text{ g}$$

As an example, the following method may be used to concurrently form and package a pre-dosed applicator as indicated in the example above, Step 1, get a container;
Step 2, insert four absorbent pads or discs and push them onto the bottom of the container and keep flat;
Step 3, using a pipette, take the desired quantity of solution, 2.84 g or 2.37 ml of 28.77% aluminum sulfate solution, and inject the solution into the bottom of the container onto the absorbent pads;
Step 4, insert 12 Q-tip brand applicators with the absorbent end or cotton side facing downward, inside the container; and
Step 5, close the lid.

The solution containing aluminum sulfate will be soaked into Q-tip brand applicators and will be maintains wet during storage.

An alternative method or procedure is to swap step 3 with step 4.

Figure 2:
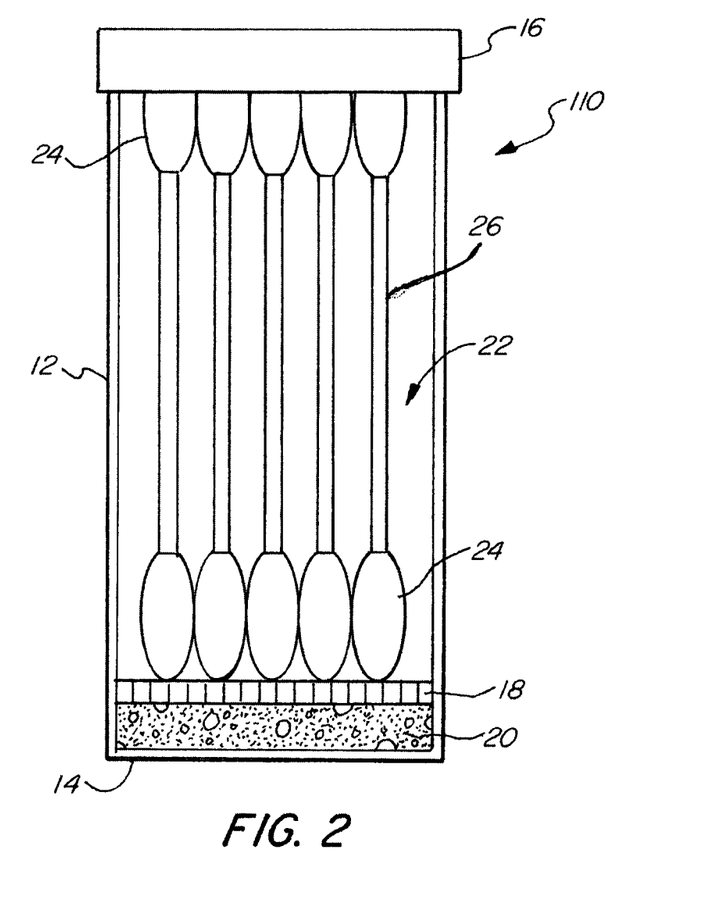
FIG. 2 schematically illustrates another embodiment of the present invention using a barrier membrane.

FIG. 2 schematically illustrates another embodiment of the present invention. The packaged pre-dosed applicators 110 in this embodiment comprise a barrier membrane 18 between the absorbent ends 24 and the absorbent pad 20. The barrier membrane 18 has a controllable porosity or permeability and may have capillaries to control the flow of fluid or solution from between the absorbent pad 20 and the absorbent end 24 of the applicator 22. The applicator 22 may have two opposing absorbent ends 24 with one of the absorbent ends 24 contacting the barrier membrane 18.

In this embodiment, once an applicator 22 is placed inside the container 12 one absorbent end 24 contacts the barrier membrane 18 and fluid passes through the barrier membrane 18 and is absorbed by the absorbent end 24. The other absorbent end 24 of the applicator 22 will remain dry. An appropriate quantity or matched quantity of fluid may be placed in the absorbent pad 20 so that when the absorbent end 24 is in contact with the absorbent pad 20 nearly all of the fluid or liquid is absorbed so that there is no free fluid or liquid in the container 12, that is all of the liquid is absorbed in the absorbent pad 20. Therefore, even if the container 12 is placed on its side or upside down no fluid or liquid will move within the container 12 or be absorbed by the opposing dry absorbent and 24 of the applicator 22.

The barrier membrane 18 may be of a woven material with predetermined weave spacing or a membrane having capillaries of a predetermined diameter so as to control the flow of fluid or liquid passing therethrough. The barrier membrane 18 controls the flow of fluid between the absorbent pad 20 and the absorbent end 24 in contact therewith. Once the absorbent end 24 contacts the barrier membrane 18 fluid or liquid flows by capillary action until the absorbent end 24 is saturated, can hold no more fluid, or is holding a predetermined quantity of fluid or liquid. The barrier membrane 18 modulates or controls the flow of fluid or liquid being absorbed by the absorbent end 24 so that a predetermined moisture or dampness may be maintained in the absorbent end 24 of the applicator 22. The flow of fluid or liquid through the barrier membrane 18 may be controlled by considering the vapor pressure and surface tension of the fluid or liquid and the material and spacing structure of the weave or diameter of the capillary of the barrier membrane 18.

The barrier membrane 18 may also serve as a hydrophobic porous or semipermeable membrane, film, or filter that may separate out liquids and permit gas or vapor or a component of the solution to pass therethrough. A liquid may be contained in the absorbent pad 20 with a gas or vapor there from being transmitted through the barrier membrane 18 to be absorbed by the absorbent end 24 of the applicator 22. This may be particularly advantageous when applying some medications that are volatile or have a low vapor pressure. This may be particularly advantageous to control the dosing in some applications, such as in the nose or on nasal membranes. This may also be advantageous when a semi permeable membrane is used that only permits a preselected component of the solution contained within the absorbent pad to pass there through. Therefore, a solvent used to contain intended material being delivered may be prevented from being absorbed by the absorbent end of the applicator. This is advantageous when a particular solvent may be needed to form the solution that is not desired to be applied with the material or solute dissolved in the solvent.

Figure 3A:
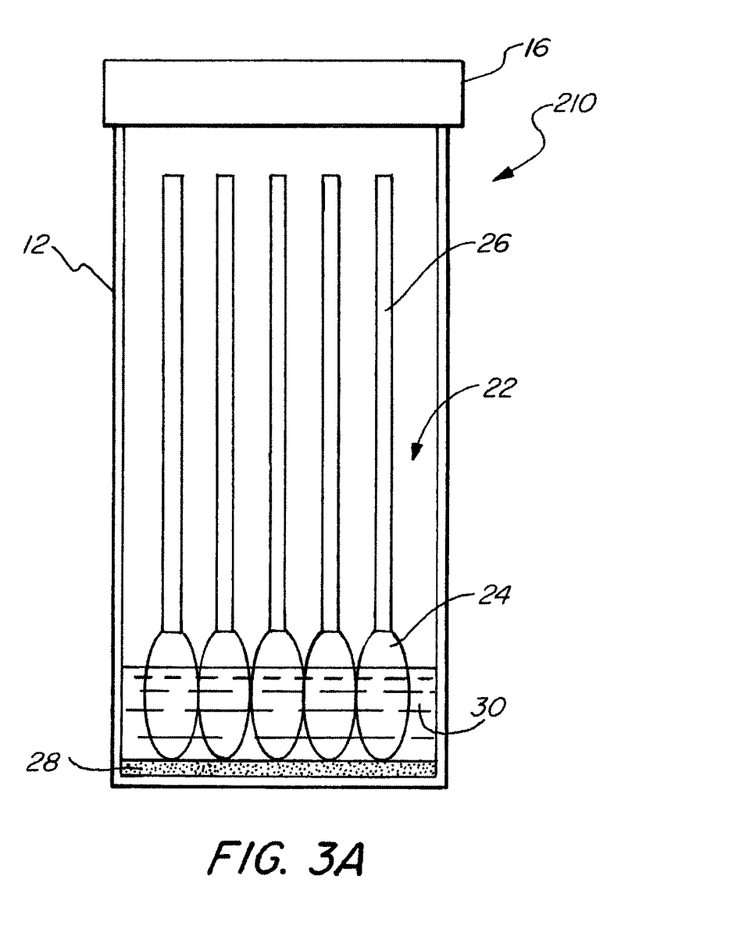
FIGS. 3A-B schematically illustrates another embodiment of the present invention using an initially compressed absorbent pad.
Figure 3B:
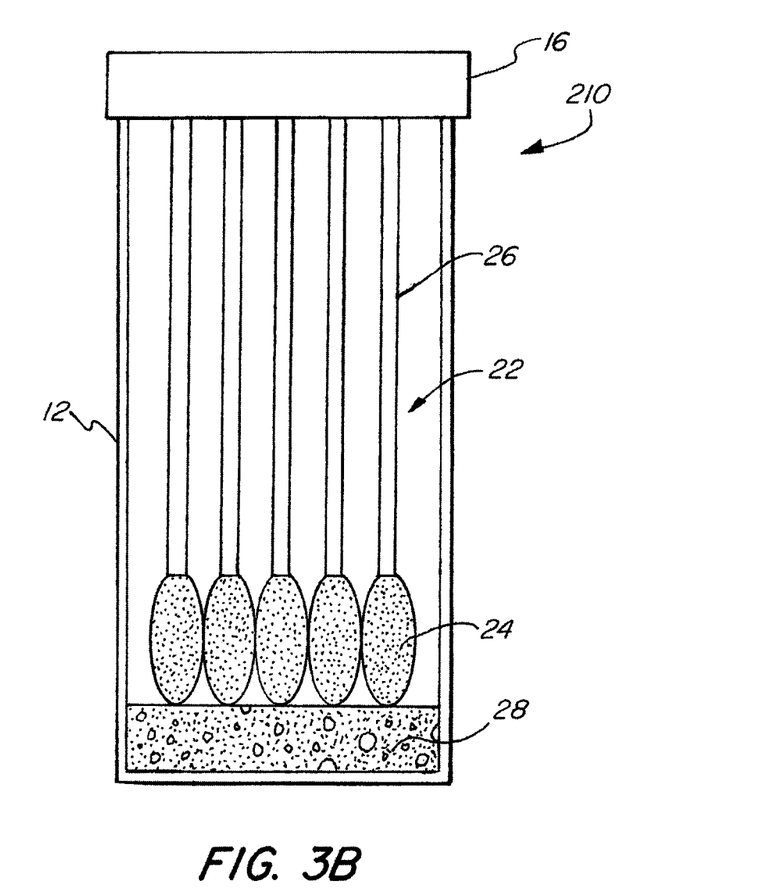

FIGS. 3A-B illustrates another embodiment of the invention of packaged pre-dosed applicators 210. In this embodiment a compressed absorbent pad 28 is used. A package 12 for containing a pre-dosed applicator comprises a compressed pad or foam material 28 placed at the bottom of the container 12, which thickness is reduced to one quarter or one third of its normal thickness when it is dry, as illustrated in FIG. 3A. During the packing process, the compressed pad 28 is placed into the container 12 first, a pre-determined number of applicators 22 are inserted into the container 12. Because the compressed absorption pad 38 is initially thinner, after the applicators 22 are placed inside the container 12, there is still a clearance at the opening end of the container between the end of the stick or handle 26. This clearance is very useful for placing the lid 16, because all of applicators are initially set lower inside the container below the top of the open end.

FIG. 3B illustrates the packaged pre-dosed applicators 210 after the compressed absorbent pad has absorbed the solution 30, illustrated in FIG. 3A. When the initially compressed absorbent pad absorbs the solution 30 it expands pushing the applicators 22 upward towards the lid 16. The ends of the stick or handle 26 may now contact the lid 16. Because the absorbent end 24 of applicator 22 often will need more time to be wetted after the solution 30 is injected into a container 12, the applicators 22 can float up to the level of the top of the solution 30. This resulting in the applicator being set too high making it hard to manage during the assembly process. By injecting the solution 30 after inserting the applicators 22, the stick or handles 26 of the applicators 22 stay below the top of the container 12 and lid 16 until the solution 30 is injected making assembly easier.

Use of the initially compressed absorption pad 28 is especially beneficial for an automatic assembly process, because the applicators 22 could pop up too high in the container and causing difficulty in closing the lid 16. After the compressed pad 28 and all of applicators 22 are placed into the container 12, a pre-dosed solution 30, which may be medicine, is injected into the container 12. The lid 16 can also be placed on the container 12 while the applicators 22 are still below the level of the open top of the container 12 and before the solution 30 is absorbed by the initially compressed absorbent pad 28.

After the lid 16 is closed, the initially compressed absorbent pad 28 will expend by absorbing the solution completing the packaging process and final dosing of the applicators 22 will occur inside the container 12 without further processing.

The initially compressed absorption pad 28 is wetted, thereafter it expands to its normal height pushing the applicators 22 against the bottom side of lid 16. The expansion of the absorption pad 28 will help to secure applicators 22 and prevent them from moving around within the container 12.

FIG. 3B illustrates the finished assembling of the packaged pre-dosed applicators 210. The stick or handle 26 of applicators 22 may contact the bottom of the lid 16, when the expanded absorption pad 28 and the absorbent end 24 of the applicators 22 are wet, but advantageously there is no excessive liquid inside the container.

Figure 4A:
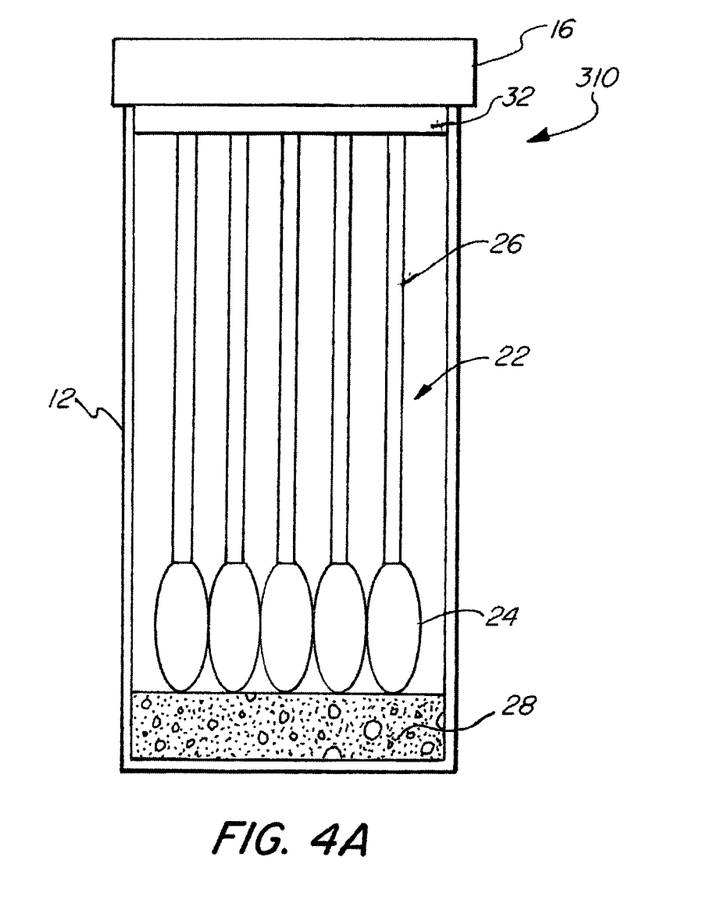
FIGS. 4A-B schematically illustrates another embodiment of the present invention using an inner lid with an opening.
Figure 4B:
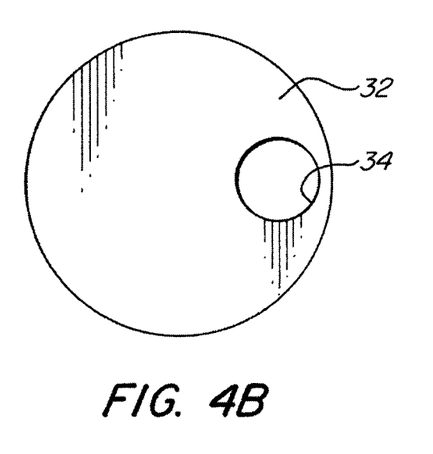

FIGS. 4A-B illustrates yet another embodiment of the invention. In this embodiment an inner lid 32 is used with an opening 34. The inner lid 32 has an opening 34 through it. This permits the applicators 22 to be dispensed through the opening 34. Use of the inner lid 32 can secure the applicators 22, but yet permit the applicators 22 to be dispensed when the container 12 is opened and tilted. The inner lid 32 also provided a secondary cover to slow down evaporation of the solution contained within the absorbent pad 28 during storage and prevents loss of moisture or liquid if the lid 16 is accidentally left opened after use.

The present invention may also comprise a single dose package, such as a container holding one to three applicators intended for use in a single dose application or on a single individual or patient.

While the present invention has been described with respect to several different embodiments, it will be obvious that various modifications may be made without departing from the spirit and scope of this invention.

What is claimed is:

1. A package for containing and dosing pre-dosed applicators comprising:
    a container having a bottom and a top with a container depth from the bottom to the top of said container;
    an absorbent pad placed adjacent the bottom, said absorbent pad having an initial dry compressed thickness and a subsequent expanded wet thickness;
    a solution containing a material placed on the absorbent pad;
    a plurality of applicators, each of said plurality of applicators having an applicator length and an absorbent end placed in the container, wherein the absorbent end is placed adjacent said absorbent pad;
    wherein the applicator length combined with the initial dry compressed thickness of said absorbent pad is less than the container depth and the applicator length combined with the subsequent expanded wet thickness of said absorbent pad is greater than the container depth; and
    a lid placed over the top of the container.

2. The package for containing and dosing pre-dosed applicators as in claim 1 wherein:
    the material comprises an antihemorrhagic agent.

3. A package for containing and dosing pre-dosed applicators comprising:
    a container having a bottom and a top;
    an absorbent pad placed adjacent the bottom;
    a solution containing a material placed on the absorbent pad;
    a plurality of applicators having an absorbent end placed in the container, wherein the absorbent end is placed adjacent said absorbent pad; and
    a barrier membrane placed between the absorbent end of said plurality of applicators and said absorbent pad
    a lid placed over the top of the container.

4. The package for containing and dosing pre-dosed applicators as in claim 3 wherein:
    said barrier membrane comprises capillaries having a predetermined diameter, wherein a flow of said solution between said absorbent pad and the absorbent end of said plurality of applicators may be controlled.

5. The package for containing and dosing pre-dosed applicators as in claim 3 wherein:
    said barrier membrane comprises a material having a weave with predetermined spacing, wherein a flow of said solution between said absorbent pad and the absorbent end of said plurality of applicators may be controlled.

6. The package for containing and dosing pre-dosed applicators as in claim 3 wherein:
    said barrier membrane is semipermeable, whereby only a vapor passes therethrough.

7. The package for containing and dosing pre-dosed applicators as in claim 3 wherein:
    said solution has a quantity matching a quantity of solution capable of being absorbed by the absorbent ends of said plurality of applicators,
    whereby no free liquid is contained in said package.

8. The package for containing and dosing pre-dosed applicators as in claim 3 wherein:
    said absorbent pad is initially compressed,
    whereby said solution causes said absorbent pad to expand.

9. The package for containing and dosing pre-dosed applicators as in claim 3 wherein:
    further comprising an inner lid having a hole placed between the top of said container and said lid.

10. A method of dosing and packaging pre-dosed applicators for dispensing a material comprising the steps of:
    placing an initially compressed absorbent pad having an initial compressed thickness and a subsequent expanded thickness in the bottom of a container, the container having a height;
    inserting a plurality of applicators having an absorbent end into the container, wherein the absorbent end contacts the initially compressed absorbent pad, each of said plurality of applicators having an applicator length;
    injecting a quantity of a solution containing the material into the container, the quantity of the solution having an initial depth when placed in the container; and
    wherein the initial compressed thickness of the initially compressed absorbent pad combined with the initial depth and the applicator length is less than the height of the container.

11. The method of dosing and packaging pre-dosed applicators for dispensing a material as in claim 10 wherein:
    the material comprises an antihemorrhagic agent.

12. The method of dosing and packaging pre-dosed applicators for dispensing a material as in claim 10 wherein:
    the quantity of the solution is adjusted as a function of a number of the plurality of applicators and a predetermined degree of wetness of the absorbent end of each of the number of the plurality of applicators.

* * * * *